US010239116B2

(12) United States Patent
Nascimento et al.

(10) Patent No.: US 10,239,116 B2
(45) Date of Patent: Mar. 26, 2019

(54) SOLVENT SYSTEM AND COMPOSITIONS THEREWITH

(71) Applicant: RHODIA POLIAMIDA E ESPECIALIDADES LTDA, Sao Paulo (SP) (BR)

(72) Inventors: Ronaldo Nascimento, Sao Paulo (BR); Suelbi Silva, Sao Paulo (BR)

(73) Assignee: RHODIA POLIAMIDA E ESPECIALIDADES LTDA, São Paulo (BR)

(*) Notice: Subject to any disclaimer, the term of this patent is extended or adjusted under 35 U.S.C. 154(b) by 29 days.

(21) Appl. No.: 14/764,604

(22) PCT Filed: Feb. 12, 2014

(86) PCT No.: PCT/IB2014/000143

§ 371 (c)(1),
(2) Date: Jul. 30, 2015

(87) PCT Pub. No.: WO2014/125357

PCT Pub. Date: Aug. 21, 2014

(65) Prior Publication Data

US 2015/0361281 A1 Dec. 17, 2015

(30) Foreign Application Priority Data

Feb. 12, 2013 (WO) .................. PCT/IB2013/000176

(51) Int. Cl.

| | |
|---|---|
| ***C09D 7/00*** | (2018.01) |
| ***B22C 1/22*** | (2006.01) |
| ***C08G 18/54*** | (2006.01) |
| ***C09D 175/04*** | (2006.01) |
| ***C08G 18/42*** | (2006.01) |
| ***C07D 317/24*** | (2006.01) |
| ***C09D 101/18*** | (2006.01) |
| ***C09D 133/00*** | (2006.01) |
| ***C09D 167/00*** | (2006.01) |
| ***C09D 179/04*** | (2006.01) |
| ***C09D 7/20*** | (2018.01) |
| *C08K 5/1565* | (2006.01) |

(52) U.S. Cl.

CPC .......... *B22C 1/2273* (2013.01); *C07D 317/24* (2013.01); *C08G 18/42* (2013.01); *C08G 18/542* (2013.01); *C09D 7/20* (2018.01); *C09D 101/18* (2013.01); *C09D 133/00* (2013.01); *C09D 167/00* (2013.01); *C09D 175/04* (2013.01); *C09D 179/04* (2013.01); *C08K 5/1565* (2013.01)

(58) Field of Classification Search

CPC ... C11B 9/0069; C11B 9/0073; C11B 9/0076; C09D 7/00; C09D 7/20; C09D 7/40; C09D 7/41; C09D 7/61; C09D 7/63

See application file for complete search history.

(56) References Cited

U.S. PATENT DOCUMENTS

| | | | | |
|---|---|---|---|---|
| 4,852,629 | A | 8/1989 | Fechter et al. | |
| 5,914,360 | A | 6/1999 | Aumuller | |
| 2006/0079600 | A1 | 4/2006 | Gopalratnam et al. | |
| 2010/0137480 | A1 | 6/2010 | Denilson et al. | |
| 2012/0129744 | A1* | 5/2012 | McDougall .......... | C10M 129/20 508/307 |

FOREIGN PATENT DOCUMENTS

| | | | |
|---|---|---|---|
| EP | 0978545 | A1 | 2/2000 |
| EP | 1074568 | A2 | 2/2001 |
| EP | 1809456 | A1 | 4/2006 |
| FR | 2950894 | A1 | 4/2011 |
| WO | WO 89/07626 | A1 | 8/1989 |
| WO | WO 91/09908 | A1 | 7/1991 |
| WO | WO 99/57217 | A1 | 11/1999 |

OTHER PUBLICATIONS

New Approach to the Synthesis of 1,3-Dioxolanes, V. B. Vol'eva et al., Russian Journal of Organic Chemistry, 2012, vol. 48, No. 5, pp. 638-641.*

New Class of Acetal Derived from Glycerin as a Biodiesel Fuel Component, Garcia et a., Energy & Fuels 2008, 22, 4274-4280.*

Anonoymous—Mono-Methyl Esters and Vinyl Esters as Aromatic Hydrocarbon and Secondary Solvent Replacements in Foundry Resin Systems; Research Disclosure, 09, 1999, vol. 425, p. 1187.

* cited by examiner

*Primary Examiner* — Haidung D Nguyen
(74) *Attorney, Agent, or Firm* — Osha Liang LLP

(57) ABSTRACT

The present invention relates to a solvent system characterized by the fact that is comprises one or more dioxolane-derived esters of formula I Formula I $$\text{(2,2-}R_1R_2\text{-1,3-dioxolan-4-yl)}-(CH_2)_n-O-C(=O)-R_3$$

where R1, R2 and R3 are the same or different, selected from hydrogen, alkyl, alkenyl and phenyl, and n is an integer between 1 and 5.

7 Claims, No Drawings

SOLVENT SYSTEM AND COMPOSITIONS THEREWITH

CROSS-REFERENCE TO RELATED APPLICATIONS

The present application is a U.S. national stage entry under 35 U.S.C. § 371 of International Application No. PCT/IB2014/000143 filed Feb. 12, 2014, which claims priority to WO Application No. PCT/IB2013/000176 filed on Feb. 12, 2013, the whole content of this application being herein incorporated by reference for all purposes.

The present invention generally concerns new solvent systems that comprise dioxolane-derived esters, as well as coating compositions comprising such systems. Such dioxolane-derived esters are more environment friendly than most commercial solvents, providing equivalent or superior performance in most coating applications as well as in foundry application.

BACKGROUND

Solvent systems are used in a very wide range of applications, typically related to paint and coatings, as coalescent agent, drying time modifier (retarder), emulsifier, solubilizer for pigments, etc. As known by the one skilled in the art, solvent systems have to be well designed to provide good solvency performance with advantageous cost/benefit ratios, but in more recent times, environment restrictions have grown, and a number of well-performing traditional solvents especially based on glycol are becoming limited and, in the limit, banned from use. Therefore the need for developing new solvent systems comprising alternative solvents is high.

BRIEF DESCRIPTION OF THE INVENTION

In view of the facts mentioned above, new solvent systems comprising the use of dioxolane ester-derivatives of formula I were devised, said dioxolane ester-derivatives being useful per se, for instance, as agent for coatings, coalescence or drying retardants in the formulation of industrial coatings, architectural or graphic. Said dioxolane ester-derivatives are also useful in foundry application. One important aspect is the fact that said dioxolane ester-derivatives are environment-friendly as originated from renewable sources and present less severe effects to the environment and human health with no losses in the quality of the coating.

Usage of this product in a formulation comprising a solvent system affords up to 70% w/w lesser amount of glycol solvents that are widely used in the prior art compositions, in particular glycol ether-based solvents, leading to an advantageous cost×benefit relation.

DESCRIPTION OF THE INVENTION

Solvent System

The invention, in a first aspect, concerns a solvent system characterized by the fact that it comprises one or more dioxolane-derived esters of formula I Formula I

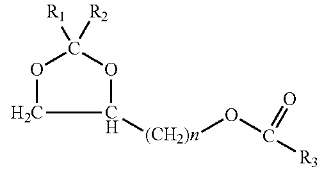

where R1, R2 and R3 are the same or different, selected from hydrogen, alkyl, alkenyl and phenyl, and n is an integer between 1 and 5.

By "solvent system" according to the present invention, it should be understood that the dioxolane-derived ester of formula I can be used alone or in combination with one or more other dioxolane-derived ester of formula I and/or one or more other solvent.

In a particular embodiment of the invention, R1, R2 and R3 are chosen among methyl, ethyl, n-propyl, isopropyl, n-butyl, isobutyl, sec-butyl, n-pentyl, isopentyl, sec-pentyl, cyclopentyl, n-hexyl, cyclohexyl, 2-methylpentyl, 3-methylpentyl or phenyl and n is 1 or 2. More preferably, R1 is methyl, R2 is chosen among methyl, isobutyl and phenyl, R3 is chosen among methyl, ethyl, n-propyl, isopropyl, n-butyl and isobutyl and n=1.

A particular dioxolane-derived ester according to the invention is 2,2-dimethyl-1,3-dioxolane-4-methanol acetate (cited herein as DDAcetate, for ease of reference, in which R1=R2=R3=CH3 and n=1), that can be derived from 2,2-dimethyl-1,3-dioxolane-4-methanol, also known as solketal.

The solvent system comprises advantageously at least a dioxolane-derived ester being 2,2-dimethyl-1,3-dioxolane-4-methanol acetate.

The solvent system according to one advantageous embodiment of the invention is a blend of at least 2 dioxolane-derived esters of formula I chosen among 2,2-dimethyl-1,3-dioxolane-4-methanol acetate, 2-methyl-2-isobutyl-1,3-dioxolane-4-methanol acetate, 2-methyl-2-benzyl-1,3-dioxolane-4-methanol acetate, 2,2-dimethyl-1,3-dioxolane-4-methanol propionate, 2-methyl-2-isobutyl-1,3-dioxolane-4-methanol propionate, 2-methyl-2-benzyl-1,3-dioxolane-4-methanol propionate, 2,2-dimethyl-1,3-dioxolane-4-methanol butyrate, 2-methyl-2-isobutyl-1,3-dioxolane-4-methanol butyrate, 2-methyl-2-benzyl-1,3-dioxolane-4-methanol butyrate, 2,2-dimethyl-1,3-dioxolane-4-methanol isobutyrate, 2-methyl-2-isobutyl-1,3-dioxolane-4-methanol isobutyrate, 2-methyl-2-benzyl-1,3-dioxolane-4-methanol isobutyrate, 2,2-dimethyl-1,3-dioxolane-4-methanol pentanoate, 2-methyl-2-isobutyl-1,3-dioxolane-4-methanol pentanoate, 2-methyl-2-benzyl-1,3-dioxolane-4-methanol pentanoate, 2,2-dimethyl-1,3-dioxolane-4-methanol isovalerate, 2-methyl-2-isobutyl-1,3-dioxolane-4-methanol isovalerate, 2-methyl-2-benzyl-1,3-dioxolane-4-methanol isovalerate.

In a preferred embodiment according to the invention, the solvent system is a blend of at least 2 dioxolane-derived esters of formula I chosen among 2,2-dimethyl-1,3-dioxolane-4-methanol acetate, 2-methyl-2-isobutyl-1,3-dioxolane-4-methanol acetate, 2-methyl-2-benzyl-1,3-dioxolane-4-methanol acetate.

In another preferred embodiment according to the invention, the solvent system is a blend of 2,2-dimethyl-1,3-dioxolane-4-methanol acetate and 2,2-dimethyl-1,3-dioxolane-4-methanol propionate.

The solvent system according to the present invention can comprise one or more other solvents chosen among esters, ketones, alcohols, aromatics, hydrocarbons and mixtures thereof.

The esters particularly preferred are alkyl esters, preferably C1-C4 alkyl acetates, notably ethyl, butyl or propyl acetates. Those esters are commercially available.

The ketones particularly preferred are alkyl ketones, preferably chosen between acetone, methylisobutylketone (MIBK), diisobutylketone (DIBK), methylethylketone (MEK), diacetone alcohol (DAA). Those ketones are commercially available.

The alcohols that can be used in the solvent system according to the present invention are chosen among alkyl alcohols, preferably C1-C6 alcohols, notably methanol, ethanol, isopropanol, butanol, methylisobutyl alcohol. Those alcohols are commercially available.

As aromatic compounds useful in the solvent system according to the present invention, we can cite xylene, toluene, light aromatic solvent naphtha (C8 to C10) sold under the name Solvesso™ 100 and Heavy Aromatic Solvent Naphtha (C10 and C10 to C13) sold under the name Solvesso™150 and Solvesso™ 200. Those aromatic compounds are commercially available.

The hydrocarbons that can be used in the solvent system according to the present invention are chosen among hexane, cyclohexane, white spirit (mixture of aliphatic and alicyclic hydrocarbons C7-C12) and naphtha mixtures. Those hydrocarbons are commercially available.

According to one embodiment, the solvent system according to the present invention has advantageously the following composition:

0.5-85%, preferably 0.5-40% and still more preferably 1-25%, by weight of dioxolane-derived esters of formula I relative to the total weight of solvents;

10-60%, preferably 20-60%, by weight of esters relative to the total weight of solvents;

10-60%, preferably 20-60%, by weight of ketones relative to the total weight of solvents;

5-30%, preferably 5-15%, by weight of alcohols relative to the total weight of solvents;

10-60%, preferably 15-50%, by weight of aromatics relative to the total weight of solvents;

10-40%, preferably 10-30% by weight of hydrocarbons relative to the total weight of solvents.

Uses of the Solvent System

The present invention also provides the use of said solvent system in coatings like paints and especially in paints based on acrylic, nitrocellulose, polyester, polyol polyester, epoxy, alkyd, melamine, maleic, phenolic resins or isocyanate-based paint as well as in polyurethane-based paint, more particularly for polyurethane-based paint. Said resins or paints are notably used in or applied as industrial, graphics and architectural paints.

A coating is generally paint, varnish, lacquer or other finish used to create a protective and/or decorative layer on a substrate.

A paint is a composition including at least a resin and a solvent. It also generally comprises additives and pigments.

A resin is a synthetic or natural material used as the binder in coatings. The resin can be translucent or transparent, solid or semi-solid.

More preferably, the solvent system according to the present invention is used in coating compositions, such as paints, and acts as coalescent agent, drying time modifier (e.g. retarder), emulsifier, thinner, diluent and solubilizer, in particular for pigments.

The solvent system can have one or more of the above actions in the coating composition but it does not participate to the polymerization of the resin. The solvent system does not react with the components of the coating composition. The solvent system evaporates and does not take part of the final product after evaporation.

As a coalescent agent, the solvent system according to the invention promotes contact between the particles, facilitating and enhancing the formation of a film on application of the paint to a substrate, thereby allowing the appearance and durability of the applied film. After the formation of the film, the solvent system evaporates and does not take part of the film.

As a drying time modifier, the solvent system according to the invention modifies (either increase or decrease) the drying time following the application of coating formulation to substrate.

As an emulsifier, the solvent system according to the invention promotes the dispersion of one phase into another when the two phases are not completely miscible.

As a thinner, the solvent according to the present invention adjusts the viscosity and the solid content.

As a solubilizer, the solvent system according to the invention can solubilize the polymers and additives useful in paints compositions, like pigments.

The solvent system according to the present invention can also be used as a solubilizer in various applications. It can solubilize grease or oily compounds, active ingredients (pesticides, herbicides, fungicides, pharmaceutical intermediates or active principles), polymers and additives (antioxidants, plasticizers, excipients, rheology modifiers, and preservatives).

The solvent system according to the present invention is advantageously used for replacing partial or total glycol-based solvents, in particular glycol ether-based solvents, in coating compositions. The present invention provides therefore the use of dioxolane-derived esters of formula I as a partial or total replacement for glycol solvent systems of coating compositions, in particular glycol ether-based solvents. According to the present invention, the solvent system based on dioxolane-derived esters of formula I advantageously replaces glycol ether solvent system based on butylglycol acetate (EGBEA), propylene glycol monomethyl ether acetate (2PG1MEA) or ethylglycol acetate (EGMEA). The solvent system according to the invention can also replace partially or totally ethyl ethoxypropionate in coating compositions.

Indeed, butylglycol acetate is irritant and harmful, some isomers of 2PG1MEA and EGMEA are dangerous for health (CMR) and it is highly recommended not to manipulate those compounds. Those solvents have also a strong odor. 2PG1MEA and EGMEA are also inflammable. Ethyl ethoxypropionate is highly inflammable and can generate peroxides.

According to the claimed invention, the amounts of the solvent system based on dioxolane-derived esters of formula I, especially the amounts of DDAcetate, that are added to coating compositions are markedly less than the amounts used with glycol ether solvent systems, especially with butylglycol acetate, propylene glycol monomethyl ether acetate, or ethylglycol acetate. The amount of the solvent system based on dioxolane-derived esters of formula I, especially the amount of DDAcetate, is preferably the half of the one of glycol ether solvent systems, especially with butylglycol acetate, propylene glycol monomethyl ether acetate or ethylglycol acetate, without any negative influence on the required effects of the coating composition. For propylene glycol monomethyl ether acetate or ethylglycol acetate, it is possible to replace up to 4 parts of one of those components by 1 part of the solvent system according to the present invention without any negative influence on the required effects of the coating composition.

Coating Compositions

The present invention also provides a coating composition comprising a solvent system based on dioxolane-derived esters of formula I, especially on DDAcetate. Said coating composition is preferably a non-water based coating. The coating composition according to the present invention can also advantageously comprise a resin, which can be chosen among acrylic resins, nitrocellulose resins, polyester resins, polyol polyester resins, epoxy resins, alkyd resins, melamine resins, maleic resins, phenolic resins, isocyanate-based resins, polyurethane-based resins. More particularly the resin is a polyurethane-based resin. In the coating composition according to the present invention, the resin represents advantageously between 3 and 50%, preferably between 10 and 20% of the total weight of the coating composition.

In a preferred embodiment, the coating composition according to the present invention does not contain glycol ether solvents, especially it does neither contain butylglycol acetate, nor propylene glycol monomethyl ether acetate nor ethylglycol acetate nor ethyl ethoxypropionate.

In the coating composition according to the present invention the solvent system can comprise one or more other solvents chosen among esters, ketones, alcohols, aromatics, hydrocarbons and mixtures thereof.

The esters particularly preferred are alkyl esters, preferably C1-C9 alkyl acetates, notably ethyl, butyl or propyl acetates. Those esters are commercially available.

The ketones particularly preferred are alkyl ketones, preferably chosen between acetone, methylisobutylketone (MIBK), diisobutylketone (DIBK), methylethylketone (MEK), diacetone alcohol (DAA). Those ketones are commercially available.

The alcohols that can be used in the solvent system according to the present invention are chosen among alkyl alcohols, preferably C1-C6 alcohols, notably methanol, ethanol, isopropanol, butanol, methylisobutyl alcohol. Those alcohols are commercially available.

As aromatic compounds useful in the solvent system according to the present invention, we can cite xylene, toluene, light aromatic solvent naphtha (C8 to C10) sold under the name Solvesso™100 and heavy aromatic solvent naphtha (C10 and C10 to C13) sold under the name Solvesso™ 150 and Solvesso™ 200. Those aromatic compounds are commercially available.

The hydrocarbons that can be used in the solvent system according to the present invention are chosen among hexane, cyclohexane, white spirit (mixture of aliphatic and alicyclic hydrocarbons C7-C12) and naphtha mixtures. Those hydrocarbons are commercially available.

In the coating composition according to the present invention, the solvent system has advantageously the following composition:

- 0.5-85%, preferably 0.5-40% and still more preferably 1-25%, by weight of dioxolane-derived esters of formula I relative to the total weight of solvents;
- 10-60%, preferably 20-60%, by weight of esters relative to the total weight of solvents;
- 10-60%, preferably 20-60%, by weight of ketones relative to the total weight of solvents;
- 5-30%, preferably 5-15%, by weight of alcohols relative to the total weight of solvents;
- 10-60%, preferably 15-50%, by weight of aromatics relative to the total weight of solvents;
- 10-40%, preferably 10-30% by weight of hydrocarbons relative to the total weight of solvents.

The coating composition according to the present invention is preferably a solvent based composition, and thus does not contain water.

The solvent system according to the present invention represents advantageously between 30 and 95%, preferably between 50 and 90% of the total weight of the coating composition.

The coating composition according to the present invention can also contain additives like pigments, dyes, carriers, fillers, dullness agents. Those compounds are well known by the skilled person in the art and generally represent between 0.5 and 3% by weight of the total weight of the coating composition.

Advantageously, the coating composition according to the present invention is a paint composition, a varnish composition, a lacquer composition or a finish composition.

The coating composition according to the present invention can be a car refinish coating composition, can coating composition, finish for leather composition, maintenance coating composition, automotive OEM coating composition, coil coating composition, finish for textile and paper composition, wood coating composition and appliance coating composition.

The coating composition according to the invention is particularly advantageous because the film formed has a high gloss, good mechanical properties and less odor when applied.

Foundry

The present invention also relates to the discovery that said solvent system according to the present invention is a useful solvent for phenolic resins in polyurethane-forming foundry binder systems, alone or as a mixture with other solvents.

The foundry application concerns the production of metal articles by molding, in particular the production of engines like motors. The molds that are needed to produce the metal articles are made by mixing a solution of phenolic resin in a solvent system with sand. Then, an isocyanate compound and eventually a curing catalyst, is added to the mixture to cure the polyurethane mold. The starting material forming the polyurethane after curing and comprising the phenolic resin and the isocyanate compound is called foundry binder system. To produce the metal article, the metal is melted and poured into the mold. In this application, the mold serves only once and is destroyed to recover the metal article once cooled.

The role of the solvent system in the foundry application is key because it is necessary to reduce the viscosity of the phenolic resin so as to allow the formation of complex shapes of molds. It is also important to have a solvent with low flammability (high flash point) and that generates fewer smokes during the curing of the polyurethane. The solvent should also be compatible with the resin, not react with the compounds of the resin, not contain nitrogen atom or hydroxyl group, has a low hygroscopicity, and few odor.

The present invention therefore provides a foundry binder system forming a curable polyurethane with a catalytically effective amount of a curing catalyst, comprising at least:

A. a phenolic resin component comprising at least:

(1) a phenolic resin; and (2) a solvent system comprising one or more dioxolane-derived esters of formula I; and B. a polyisocyanate component.

In one particular embodiment, the solvent system (2) of the phenolic resin component A is a mixture of solvents containing said one or more dioxolane-derived esters of formula I and at least another solvent for phenolic resin.

Said solvent system preferably comprises from 10 to 80% by weight, more preferably from 10 to 55% and in particular from 25 to 55% by weight of dioxolane-derived esters of formula I.

Appropriate additional solvents for phenolic resins preferably used in the solvent system are aromatic hydrocarbons such as benzene, alkylbenzenes such as toluene, xylene (meta or para), ethylbenzene, or mixtures of aromatic solvents like Solvesso™ 100, Solvesso™ 150 or Solvesso™200.

Another suitable solvent system for phenolic resins, without excluding any other, comprises one or more dioxolane-derived esters of formula I and esters such as those that are known and generally used in this type of application, in particular dimethyl esters. Examples that may be mentioned include dioctyl adipate and propylene glycol monomethyl ether acetate (WO 89/07626), dibasic esters (WO 91/09908); ethyl acetate (EP 1 809 456); methyl decanoate, methyl undecanoate and vinyl decanoate (RD425045); 1,2-diisobutyl phthalate, dibasic esters and butyldiglycol acetate (EP 1 074 568), and dialkyl esters (U.S. Pat. No. 4,852,629).

Another particular suitable mixture of solvents for phenolic resins according to the present invention, without excluding any other, comprises triacetin and a mixture of dimethyl esters, for example the product sold by Rhodia under the brand name Rhodiasolv RPDE, comprising dimethyl adipate (RN 627-93-0), dimethyl glutarate (RN1119-40-0) and dimethyl succinate (RN 106-65-0), also used as phenolic resin solvent that is useful in polyurethane-forming foundry binder systems, in particular in the no-bake or cold-box process.

Without, however, excluding the others, the appropriate proportions between the triacetin solvent and the said mixture of dimethyl ester ranges from 1:20 to 20:1.

The phenolic resin component A of the present invention is used as a solution in dioxolane-derived ester(s) of formula I, per se or with cosolvents (for example as described above).

The appropriate phenolic resins (1) are those that are known to a person skilled in the art, which are solid or liquid, but soluble in organic solvents. The concentration of solvents in component A in general may be up to 60% by weight of the resin solution, and is typically in the range from 10% to 50%, preferably from 10 to 45%, notably from 20 to 45%, even from 20 to 40% and preferably from 10% to 30%. These resins predominantly contain bridges connecting the phenolic nuclei of the polymer, which are ortho-ortho benzyl ether bridges. Generally, the resins are prepared by reacting an aldehyde and a phenol in an aldehyde/phenol mole ratio of from 1.3:1 to 2.3:1 in the presence of a metal-ion catalyst. As example of commercially available resin useful as phenolic resin (1) according to the present invention, Novolac can be cited.

The polyisocyanate component B of the binder system according to the present invention comprises a polyisocyanate, advantageously a solvent for polyisocyanates and optional ingredients. The polyisocyanate has a functionality of two or more, preferably from 2 to 5. It may be aliphatic, cycloaliphatic or aromatic, or a hybrid polyisocyanate. The polyisocyanates may also be protected polyisocyanates, polyisocyanate prepolymers and polyisocyanate quasi-prepolymers. Mixtures of polyisocyanates are also covered by the present invention. The polyisocyanate component of the foundry binder comprises a polyisocyanate, generally an organic polyisocyanate, and an organic solvent, generally comprising aromatic hydrocarbons, such as benzene, and/or alkylbenzenes like toluene or (meta or para) xylene, in amounts typically ranging from 1% by weight to about 80% by weight, relative to the weight of the polyisocyanate. Representative examples of polyisocyanates used in the present invention are aliphatic polyisocyanates such as hexamethylene diisocyanate, alicyclic polyisocyanates such as 4,4'-dicyclohexylmethane diisocyanate, and aromatic polyisocyanates such as 2,4- and 2,6-toluene diisocyanate, diphenylmethane diisocyanate, and the dimethyl derivatives thereof. Other examples of polyisocyanates are 1,5-naphthalene diisocyanate, triphenylmethane triisocyanate, and the methyl derivatives thereof, polymethylenepolyphenyl isocyanates, chlorophenylene 2,4-diisocyanate, etc.

The polyisocyanates are used in concentrations that are sufficient to bring about curing of the resin after passage of the gas or when in contact with the liquid curing catalyst.

In general, the ratio between the isocyanate group and the hydroxyl group of the phenolic resin is from 1:1 to 1:3. The amount of polyisocyanate used is generally from 10% to 500% by weight relative to the weight of the phenolic resin.

In accordance with the binder system according to the invention, the term "catalytically effective amount of a curing catalyst" means a concentration of the catalyst preferentially between 0.2% and 5.0% by weight of the phenolic resin.

Suitable curing catalysts are liquid amine curing catalysts. The useful liquid amine curing catalysts have a pKb value generally of the order of 7 to 11. Particular examples of these amines that may be mentioned include 4-alkylpyridines, isoquinoline, arylpyridines, 1-methylbenzimidazole and 1,4-thiazine. A liquid tertiary amine that is particularly used as catalyst is an aliphatic tertiary amine such as tris(3-dimethylamino)propylamine. In general, the concentration of the liquid amine catalyst ranges from 0.2% to 5.0% by weight of the phenolic resin, in particular from 1.0% to 4.0% by weight and more particularly from 2.0% to 3.5% by weight relative to the weight of the phenolic resin (polyether polyol).

Catalysts such as triethylamine or dimethylethylamine are used in a range of from 0.05% to 0.15% by weight relative to the weight of the binder. Curing via the no-bake process is performed by mixing a liquid amine curing catalyst into the foundry binder system, which is then shaped, and cured.

Process for Producing the Solvent

The dioxolane-derived esters of formula I can be prepared by esterification of the corresponding carboxylic acids with the corresponding alcohols.

A preferred process to manufacture the dioxolane-derived esters of formula I above described, is a transesterification reaction by reacting a dioxolane compound of formula II with an ester of formula III catalysed by the addition of a base catalyst, for example potassium or sodium carbonate, titanate or methanoate. The ester of formula III corresponds to formula $R_3COOR$, where $R_3$ has the same meaning as described above in formula I and R is an alkyl, preferably a C1-C6 alkyl, notably ethyl.

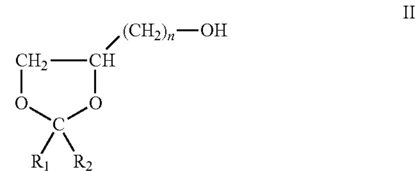

In formula II, R1, R2 and n have the same meaning as the ones described above.

The reaction of transesterification takes place advantageously at a temperature ranging from 50 to 200° C., preferably from 70 to 160° C. and at a pressure ranging from 0.5 to 1.5 bars, preferably under atmospheric pressure.

According to a preferred embodiment of the invention, the base catalyst is added in a amount ranging from 1 to 10% by weight relative to the weight of compound II as starting material, preferably from 1 to 3% by weight.

The molar ratio between the ester of formula II and the compound of formula II is from 0.5 to 2.

The reactor used to produce the dioxolane-derived esters of formula I is preferably a stirred sealed batch reactor, provided with a double envelop heat exchanger and previously flushed with an inert gas like nitrogen.

The vapors recovered at the top of the reactor are condensed.

The dioxolane-derived ester of formula I as recovered can be purified by any mean know by the skilled person in the art, advantageously by distillation.

Advantages

A particular advantage of the system solvent according to the invention is based on the fact that it presents a low evaporation rate: it remains at the final step of solvents evaporation. In coatings, the solvent system is responsible for the leveling of the film, assuring the quality of the film formation. The solvent system is also odorless and not flammable. The solvent system has also the advantage to be environment-friendly as originated from renewable sources and present less severe effects to the environment and human health.

EXAMPLES

The following examples are given only as particular embodiments of the invention, imposing no limitations to it other than the ones contained in the attached claims.

Example 1

Preparation of 2,2-dimethyl-1,3-dioxolane-4-methanol acetate ($R1=R2=R3=CH_3$ and n=1 in Formula I Corresponding to DDAcetate)

DDAcetate is prepared by transesterification reaction of ethylacetate and 2,2-dimethyl-1,3-dioxolane-4-methanol. This transesterification reaction is carried out at 90-154° C. at atmospheric pressure. The synthesis is implemented with a molar ratio (ethyl acetate/2,2-dimethyl-1,3-dioxolane-4-methanol)=1.2. Potassium carbonate ($K_2CO_3$) is used as catalyst (0.02 wt (2% by weight) based on 2,2-dimethyl-1,3-dioxolane-4-methanol). The thermodynamic equilibrium of reaction is displaced by the ethanol removal, ethanol being produced during the transesterification reaction.

83.9% of 2,2-dimethyl-1,3-dioxolane-4-methanol is converted to DDAcetate. The ethyl acetate and the excess of 2,2-dimethyl-1,3-dioxolane-4-methanol were removed by distillation. DDAcetate is separated and purified by distillation under reduced pressure (15-20 mbar, distillation range: 103-106° C.).

Example 2

DDAcetate can Replace Butylgylcol Acetate in Terms of Solubility and Evaporation Performances with Several Resins The solubility of DDAcetate was compared to the solubility of butylglycol acetate in several resins used in solvent-based coatings, such as polyester, nitrocellulose, polyurethane systems (polyurethane being the result of the reaction of polyol polyester with isocyanate), acrylic and melamine. Butylglycol acetate is used as benchmark due to its application in a wide range of commercial formulations in the paint market.

The values cited in tables I below are the result of computer simulations of Hildebrand and Hansen solubility parameters.

Specifically, as is known to those skilled in the art, the cohesion energy parameters most widely used for the characterization of solvents are those developed by Hansen (for example in the book "Hansen Solubility Parameters: A user's handbook" Hansen, Charles Second Edition 2007 Boca Raton, Fla., United States. CRC Press). There are three figures which, together, are known as the HSP. They fully describe the way in which a solvent behaves relative to that which is dissolved if their HSP values are known or can be estimated:

δD—the dispersion energy of the bonds between the molecules

δP—the energy of the intermolecular dipolar force between molecules

δH—the energy of hydrogen bonds between molecules.

Hansen demonstrated that the substances are characterized by δD, δP and δH.

The technique for determining the solubility parameters D, P and H of a substance, namely a resin in this example, consists in testing the solubility of the said substance in a series of pure solvents that belong to different chemical groups (for example hydrocarbons, ketones, esters, alcohols and glycols). The evaluation is made by considering the solvents that fully or partially dissolve or that do not dissolve the substance to be dissolved. The Solsys® software makes it possible to determine the solubility volume of the substance and, as a consequence, it makes it possible to determine the best solvent for dissolving the substance. The solubility volume is represented by a sphere (three-dimensional system) whose centre corresponds to a "normalized distance" equal to 0 and reflects the solubility maximum. All the points located on the surface of the sphere correspond to a "normalized distance" equal to 1 and reflect the solubility limit. The sphere is represented on a graph whose axes correspond to δD, δP and δH. The solubility of the resin in the solvent will be proportionately greater the closer the solubility volume is to the centre (normalized distance equal to 0). Beyond the surface of the sphere (normalized distance equal to 1), the resin is no longer soluble in the solvent.

The "normalized distance" values are used to evaluate the solubilizing power of a substance, namely of the phenolic resin in the present case, in a solvent.

TABLES I

SOLUBILITY PERFORMANCE AND EVAPORATION RATE COMPARATIVE PERFORMANCE

| Solvents | Solvent Concentration % w/w | |
|---|---|---|
| Butylglycol Acetate | 100.0 | — |
| DDAcetate | — | 100.0 |
| Total | 100.0 | 100.0 |
| **Solubility Parameters** | **Butylglycol acetate** | **DDAcetate** |
| δD | 14.00 | 13.90 |
| δP | 8.20 | 5.00 |
| δH | 8.60 | 13.00 |

TABLES I-continued

| SOLUBILITY PERFORMANCE AND EVAPORATION RATE COMPARATIVE PERFORMANCE | | |
|---|---|---|
| Standard | Butylglycol acetate | DDAcetate |
| Acrylic Standard | | |
| Initial Normalized Distance | 0.13 | 0.16 |
| Nitrocellulose Standard | | |
| Initial Normalized Distance | 0.80 | 1.06 |
| Polyester Standard | | |
| Initial Normalized Distance | 1.00 | 1.15 |
| Polyol Polyester | | |
| Initial Normalized Distance | 0.64 | 0.69 |
| Isocyanate Standard | | |
| Initial Normalized Distance | 0.19 | 0.35 |
| Melamine Standard | | |
| Initial Normalized Distance | 0.11 | 0.19 |

| Evaporation Rate (Butyl Acetate = 100) | |
|---|---|
| Butylglycol acetate | DDAcetate |
| 3.7 | 1.8 |

The results above show similar initial normalized distances, when comparing butylglycol acetate and DDAcetate, when used with several resins. Those similar values indicate the adequacy of DDAcetate when replacing butylglycol acetate. The difference between both evaporation rates can be adjusted by reformulating the solvent system, as known to the person skilled in the art. DDAcetate demonstrates a lower evaporation rate than the one of butylglycolacetate: DDAcetate present in a coating composition leads to a better quality of the film formation.

Example 3

Less DDAacetate is Necessary to Obtain Similar Performances as for Butyl Glycol Acetate Compositions in Several Resins The comparative performance between a solvent system containing butylglycol acetate with another solvent system where butylglycol acetate was replaced by DDAcetate is listed in Tables II. The glycol was successfully replaced by a smaller amount of DDAcetate, when reformulated with other solvents.

TABLES II

| COMPARATIVE SOLVENT SYSTEM PERFORMANCE EVALUATION | | |
|---|---|---|
| | Solvents Concentration % w/w | |
| | Comparative 1 | Invention 1 |
| Solvents | | |
| Ethyl Acetate | 15.0 | 15.0 |
| Butyl Acetate | 40.0 | 40.0 |
| Xylene | 42.0 | 43.5 |
| Butylglycol Acetate | 3.0 | — |
| DDAcetate | — | 1.5 |
| Total | 100.0 | 100.0 |

TABLES II-continued

| COMPARATIVE SOLVENT SYSTEM PERFORMANCE EVALUATION | | |
|---|---|---|
| | Solvents Concentration % w/w | |
| | Comparative 1 | Invention 1 |
| Solubility Parameters | | |
| δD | 16.22 | 16.26 |
| δP | 4.65 | 4.56 |
| δH | 4.86 | 4.83 |
| Acrylic Standard | | |
| Initial Normalized Distance | 0.23 | 0.24 |
| Nitrocellulose Standard | | |
| Initial Normalized Distance | 0.90 | 0.91 |
| Polyester Standard | | |
| Initial Normalized Distance | 0.68 | 0.68 |
| Polyol Polyester | | |
| Initial Normalized Distance | 1.03 | 1.04 |
| Isocyanate Standard | | |
| Initial Normalized Distance | 0.28 | 0.29 |
| Melamine Standard | | |
| Initial Normalized Distance | 0.05 | 0.05 |

As shown in the data above, when the solvent solubility performance of the solvent system containing DDAcetate is tested in several resins, such as polyester, nitrocellulose, acrylic, melamine or polyurethane systems, the behavior of the solvent system using only 1.5% w/w of DDAcetate is similar to the one using 3% w/w of butylglycol acetate.

Example 4

Less DDAacetate is Necessary to Obtain Similar Performances as for Butyl Glycol Acetate Compositions in Polyurethane Top Coat Formulations This example concerns a car refinishing formulation, where a 35% solids varnish top coat 2K (two-component, aliphatic isocyanate and polyol-polyester resins), was prepared in the laboratory, and the solvent systems used are described below in table III.

TABLE III

| COMPOSITION OF SOLVENT SYSTEMS | | |
|---|---|---|
| | Solvents Concentration % w/w (**) | |
| Solvents | Comparative 2 | Invention 2 |
| Ethyl acetate | 15.0 | 15.0 |
| Butyl acetate | 40.0 | 40.0 |
| Xylene | 42.0 | 43.5 |
| Butylglycol acetate | 3.0 | — |
| DDAcetate | — | 1.5 |
| TOTAL | 100.0 | 100.0 |

(**) solvent systems correspond to 65% w/w of the varnish formulation.

As seen, 1.5% w/w DDAcetate is used in the solvent system according to Invention 2, in comparison with the comparative 2 that comprises 3% w/w butylglycol acetate.

The formulations were applied on a metallic substrate in order to evaluate the following aspects (test methods are known per se):

a) Drying time of the film on metal substrate to evaluate the drying performance, with results being presented as a function of time, namely:

Dust free: moment when the surface no longer retains dust.

Touch-free: time when the surface subjected to the touch no longer presents grip.

Handling dry: time when the surface subjected to pressure no longer has strain.

b) Gloss: This parameter, measured with a glossmeter, compares the gloss of the surface finishing with a "mirror" standard. The test defines the degree to which the finish of the surface approaches a theoretical ideal specular gloss, based on an arbitrary value of 100 (total reflectance of the light). The brighter the sample, the higher is the result of the measurement from the glossmeter.

c) Mechanical strength and chemical resistance: this measurement defines the degree of resistance of the surface after finishing to compression movements, expressed in cycles, using in the mechanical strength test a polish and in the chemical resistance test the solvent methylethyl ketone (MEK).

d) Brookfield viscosity of the formulation—this test is performed by using a Brookfield viscometer LV DV II. This is an important parameter for determining the applicability of the paint. It has to be adequate to make an easy spreading of the film, avoiding sliding and performance problems due to low thickness of the film formed.

Tables IV below brings a comparative solvent system performance evaluation with the formulation described herein:

TABLES IV

COMPARATIVE SOLVENT SYSTEM PERFORMANCE EVALUATION

| | Comparative 2 | Invention 2 |
|---|---|---|
| Drying Time | | |
| Dust Free (min) | 14 | 15 |
| Touch Free (hours) | 04:05 | 04:10 |
| Handling dry (hours) | >8 | >8 |
| Gloss | | |
| 20° | 79.4 | 78.9 |
| 60° | 91.2 | 91.8 |
| 80° | 94.8 | 94.0 |
| Resistance | | |
| Chemical | good | good |
| Mechanical | good | good |

| Brookfield Viscosity (cps) | |
|---|---|
| Comparative 2 | 14.6 |
| Invention 2 | 13.9 |

The data above shows that even when lower amounts of the DDAcetate is used in relation to a glycol solvent in an formulation, the performance in all tested aspects is equivalent, particularly when compared with the solvent butylglycol acetate.

Example 5.1

Better Gloss and Drying Time for Compositions Wherein DDAcetate Substitute 2PG1MEA This example concerns two different coating compositions, Polyester base coat Varnish top coat 2K (two-component, aliphatic isocyanate and polyol-polyester resins), that were prepared in the laboratory, and the solvent systems used are described below in table V.

TABLE V

COMPOSITION OF SOLVENT SYSTEMS

| | Solvents Concentration % w/w (**) | |
|---|---|---|
| Solvents | Comparative 3 | Invention 3 |
| Butyl acetate | 31.0 | 36.5 |
| 2PG1MEA | 14.0 | — |
| Xylene | 26.0 | 31.0 |
| Solvesso ™ 100 | 13.0 | 13.0 |
| Ethanol | 16.0 | 16.0 |
| DDAcetate | — | 3.5 |
| TOTAL | 100.0 | 100.0 |

(**) solvent systems correspond to 85% w/w of the compositions.

Each composition is coated onto a metallic substrate (25 $g/m^2$) and the solvent system is evaporated under the following conditions:

Temperature: 5° C.

Humidity: 90%

Air speed: 0.0667 m/s

The solubility parameters and performances of the compositions are as shown in tables VI, VI.1 and VI.2:

TABLE VI

SOLUBILITY PARAMETERS

| Solubility Parameters | Comparative 3 | Invention 3 |
|---|---|---|
| δD | 16.15 | 16.17 |
| δP | 5.06 | 4.90 |
| δH | 6.91 | 6.49 |

Base Coat—Polyester

TABLE VI.1

COMPARATIVE SOLVENT SYSTEM PERFORMANCE EVALUATION

| | Comparative 3 | Invention 3 |
|---|---|---|
| Drying Time | | |
| Dust Free (min) | 14 | 10 |
| Gloss | | |
| 20° | 2.20 | 4.40 |
| 60° | 14.5 | 31.50 |
| 85° | 28.60 | 47.60 |

Top Coat—Varnish Polyurethane 2K

TABLE VI.2

| COMPARATIVE SOLVENT SYSTEM PERFORMANCE EVALUATION | | |
|---|---|---|
| | Comparative 3 | Invention 3 |
| Drying Time | | |
| Drying time | 3 h 01 | 2 h 57 |
| Gloss | | |
| 20° | 81.10 | 84.10 |
| 60° | 93.40 | 93.50 |
| 85° | 98.20 | 98.30 |

The solvent system according to the present invention provides a better gloss than the solvent system comprising 2PG1MEA, in particular in the case of the polyester base coat.

Example 5.2

Better Gloss and Drying Time for Compositions Wherein DDAcetate Substitute 2PG1MEA and Butylgylcol Acetate This example concerns two different coating compositions, Polyester base coat Varnish top coat 2K (two-component, aliphatic isocyanate and polyol-polyester resins), that were prepared in the laboratory, and the solvent systems used are described below in table VII.

TABLE VII

| COMPOSITION OF SOLVENT SYSTEMS | | |
|---|---|---|
| | Solvents Concentration % w/w (**) | |
| Solvents | Comparative 4 | Invention 4 |
| Toluene | 15.0 | 19.0 |
| Butyl acetate | 18.0 | 26.0 |
| Butylglycol acetate | 8.0 | — |
| 2PG1MEA | 21.0 | — |
| Xylene | 28.0 | 32.0 |
| Solvesso ™ 100 | 10.0 | 10.0 |
| DDAcetate | — | 13.0 |
| TOTAL | 100.0 | 100.0 |

(**) solvent systems correspond to 85% w/w of the varnish formulation.

Each composition is coated onto a metallic substrate (25 g/m$^2$) and the solvent system is evaporated under the following conditions:

Temperature: 5° C.

Humidity: 90%

Air speed: 0.0667 m/s

The solubility parameters and performances of the compositions are as shown in tables VIII, VIII.1 and VIII.2:

TABLE VIII

| SOLUBILITY PARAMETERS | | |
|---|---|---|
| Solubility Parameters | Comparative 4 | Invention 4 |
| δD | 16.15 | 16.17 |
| δP | 5.06 | 4.90 |
| δH | 6.91 | 6.49 |

Base Coat—Polyester

TABLE VIII.1

| COMPARATIVE SOLVENT SYSTEM PERFORMANCE EVALUATION | | |
|---|---|---|
| | Comparative 4 | Invention 4 |
| Drying Time | | |
| Dust Free (min) | 14 | 10 |
| Gloss | | |
| 20° | 2.20 | 4.40 |
| 60° | 14.5 | 31.50 |
| 85° | 28.60 | 47.60 |

Top Coat—Varnish Polyurethane 2K

TABLE VIII.2

| COMPARATIVE SOLVENT SYSTEM PERFORMANCE EVALUATION | | |
|---|---|---|
| | Comparative 4 | Invention 4 |
| Drying Time | | |
| Drying time | 3 h 01 | 2 h 57 |
| Gloss | | |
| 20° | 81.10 | 84.10 |
| 60° | 93.40 | 93.50 |
| 85° | 98.20 | 98.30 |

The solvent system according to the present invention provides a better gloss than the solvent system comprising 2PG1MEA and Butylglycol acetate, in particular in the case of the polyester base coat.

Example 6

Foundry Application

This example represents a particular embodiment of the invention when DDAcetate is used as a co-solvent for phenolic resin in polyurethane-forming foundry binder systems. Table IX.2 below shows the solubility parameters for a comparative solvent system (called Comparative 5) relative to solvents systems comprising DDAcetate (called Invention 5 and Invention 6). The compositions of the solvent systems are given in table IX.1. The normalized distances were obtained for a phenolic urethane resin.

TABLE IX.1

| COMPOSITIONS OF SOLVENT SYSTEMS | | | |
|---|---|---|---|
| | Solvent concentration % w/w | | |
| Solvents | Comparative 5 | Invention 5 | Invention 6 |
| Dibasic Esters (RPDE) | 59.6 | 49.6 | 25.7 |
| Solvesso ™ 100 | 26.8 | 26.8 | 40.7 |

TABLE IX.1-continued

COMPOSITIONS OF SOLVENT SYSTEMS

| Solvents | Solvent concentration % w/w | | |
|---|---|---|---|
| | Comparative 5 | Invention 5 | Invention 6 |
| Solvesso ™ 150 | 13.6 | 13.6 | 7.9 |
| DDAcetate | — | 10.0 | 25.7 |
| Total | 100.0 | 100.0 | 100.0 |

The general formula for the solvent RPDE is given below.

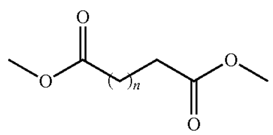

Dimethyl succinate: n=1; Dimethyl glutarate: n=2; Dimethyl adipate: n=3.

Solvesso™ 100 and Solvesso™ 150 are aromatic solvents.

TABLE IX.2

SOLUBILITY PARAMETERS

| Solubility Parameters | Comparative 5 | Invention 5 | Invention 6 |
|---|---|---|---|
| δD | 16.64 | 16.34 | 15.78 |
| δP | 3.97 | 3.99 | 4.07 |
| δH | 6.15 | 6.45 | 6.19 |
| Normalized distance | 0.45 | 0.45 | 0.46 |
| Viscosity (second) | 71" | 72" | 71" |

As is seen, the solubility parameter values for the classical mixture of commercial solvents (RPDE+Solvesso™) are similar to those obtained for the solvent systems comprising DDAcetate. This means that the solvents can be partially or totally interchangeable for the foundry application. The normalized distances are also very similar. The viscosity is not affected by the presence of DDAcetate.

The information contained in the foregoing, as well as in the examples, allows a person skilled in the art to perform alternative embodiments not expressly described, but which perform the functions taught herein with the results substantially as revealed herein. Such equivalent embodiments are encompassed by the scope of the invention and are therefore covered by the claims presented further on.

The invention claimed is:

1. A coating composition comprising a solvent system, wherein the solvent system comprises:

0.5-85% by weight of one or more dioxolane-derived esters of formula I relative to the total weight of the solvent system:

Formula I

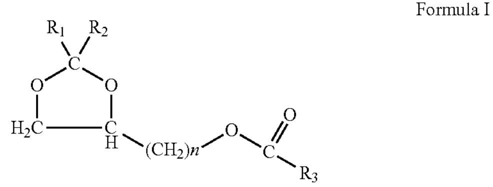

wherein $R_1$, $R_2$ and $R_3$ are the same or different, and are selected from the group consisting of methyl, ethyl, n-propyl, isopropyl, n-butyl, isobutyl, sec-butyl, n-pentyl, isopentyl, sec-pentyl, cyclopentyl, n-hexyl, cyclohexyl, 2-methylpentyl, 3-methylpentyl and phenyl, and wherein n is either 1 or 2.

10-60% by weight of esters relative to the total weight of the solvent system, wherein the esters are selected from the group consisting of $C_1$-$C_4$ alkyl acetates; and one or more of the following components:

10-60% by weight of ketones relative to the total weight of the solvent system; and/or 5-30% by weight of alcohols relative to the total weight of the solvent system; and/or 10-60% by weight of aromatics relative to the total weight of the solvent system; and/or 10-40% by weight of hydrocarbons relative to the total weight of the solvent system.

2. The coating composition according to claim 1, wherein the composition is non-water based.

3. The coating composition according to claim 1, wherein the composition does not contain glycol ether solvents.

4. The coating composition according to claim 1, further comprising a resin selected from the group consisting of acrylic resins, nitrocellulose resins, polyester resins, polyol polyester resins, epoxy resins, alkyd resins, melamine resins, maleic resins, phenolic resins, isocyanate-based resins, and polyurethane-based resins.

5. The coating composition according to claim 1, wherein the solvent system is present between 30 and 95% by weight.

6. The coating composition according to claim 1, further containing additives selected from the group consisting of pigments, dyes, carriers, fillers, and dullness agents.

7. The coating composition according to claim 1, wherein the coating composition is selected from the group consisting of a paint composition, a varnish composition, a lacquer composition and a finish composition.

* * * * *